US009466137B2

(12) United States Patent
Zhang et al.

(10) Patent No.: US 9,466,137 B2
(45) Date of Patent: Oct. 11, 2016

(54) SPIRAL CT SYSTEMS AND RECONSTRUCTION METHODS

(71) Applicants: Nuctech Company Limited, Beijing (CN); Tsinghua University, Beijing (CN)

(72) Inventors: Li Zhang, Beijing (CN); Zhiqiang Chen, Beijing (CN); Le Shen, Beijing (CN); Yuxiang Xing, Beijing (CN); Xin Jin, Beijing (CN); Qingping Huang, Beijing (CN)

(73) Assignees: Nuctech Company Limited, Beijing (CN); Tsinghua University, Beijing (CN)

( * ) Notice: Subject to any disclaimer, the term of this patent is extended or adjusted under 35 U.S.C. 154(b) by 0 days.

(21) Appl. No.: 14/708,866

(22) Filed: May 11, 2015

(65) Prior Publication Data
US 2015/0332486 A1   Nov. 19, 2015

(30) Foreign Application Priority Data

May 14, 2014   (CN) .......................... 2014 1 0202941

(51) Int. Cl.
G06K 9/00 (2006.01)
G06T 11/00 (2006.01)
A61B 6/03 (2006.01)
A61B 6/02 (2006.01)
A61B 6/00 (2006.01)
G06T 7/00 (2006.01)

(52) U.S. Cl.
CPC ............ *G06T 11/006* (2013.01); *A61B 6/027* (2013.01); *A61B 6/032* (2013.01); *A61B 6/4085* (2013.01); *A61B 6/4266* (2013.01); *A61B 6/5205* (2013.01); *G06T 7/0012* (2013.01); *G06T 2207/10081* (2013.01); *G06T 2207/30004* (2013.01); *G06T 2211/421* (2013.01)

(58) Field of Classification Search
CPC combination set(s) only.
See application file for complete search history.

(56) References Cited

U.S. PATENT DOCUMENTS

| 5,841,141 | A * | 11/1998 | Gullberg | G06T 1/1642 250/363.03 |
| 6,301,325 | B1 * | 10/2001 | Besson | A61B 6/032 378/15 |
| 7,340,028 | B2 * | 3/2008 | Grass | A61B 6/032 378/8 |
| 7,418,073 | B2 * | 8/2008 | Schlomka | A61B 6/032 378/6 |

(Continued)

*Primary Examiner* — Anand Bhatnagar
(74) *Attorney, Agent, or Firm* — Barley Snyder

(57) ABSTRACT

The present disclosure discloses a spiral CT system and a reconstruction method thereof. In some embodiments, it is proposed that data missing due to a large pitch is compensated by weighting the complementary projection data of the projection data obtained using the spiral CT system. After the data is complemented, the projection data is rebinned as cone parallel beam data, cone-angle cosine weighting and one-dimensional filtering are implemented on the rebinned data, and parallel beam back projection is finally implemented on the filtered data, to obtain the reconstructed images. In some embodiments, with the above method, the speed of the belt can be increased by more than one time in a case that the existing area of the detectors and the existing speed of the slip ring are unchanged, thereby improving the pass rate of the luggage and maintaining the quality of the reconstructed images unchanged.

5 Claims, 5 Drawing Sheets

(56) References Cited

U.S. PATENT DOCUMENTS

| | | | |
|---|---|---|---|
| 7,672,490 B2* | 3/2010 | Kohler | G06T 11/005 378/4 |
| 7,778,387 B2* | 8/2010 | Koehler | G06T 11/006 378/15 |
| 7,978,810 B2* | 7/2011 | Schwarz | G06T 11/006 378/19 |
| 8,306,304 B2* | 11/2012 | Noo | A61B 6/032 378/15 |
| 8,824,760 B2* | 9/2014 | Dennerlein | G06T 11/006 382/131 |
| 2006/0062346 A1* | 3/2006 | Grass | A61B 6/032 378/4 |
| 2007/0019776 A1* | 1/2007 | Bontus | A61B 6/032 378/4 |
| 2007/0177713 A1* | 8/2007 | Kohler | G06T 11/005 378/4 |
| 2010/0054565 A1* | 3/2010 | Quinto | G01N 23/046 382/131 |
| 2011/0052021 A1* | 3/2011 | Noo | A61B 6/032 382/131 |

* cited by examiner

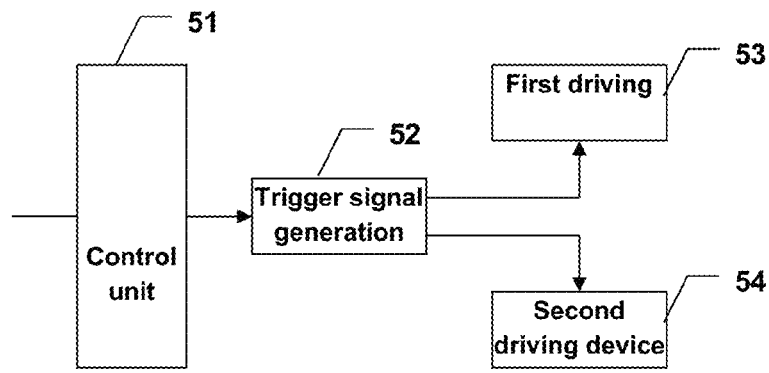

Fig. 5

S61: A MINIMUM ROW NUMBER OF DETECTORS REQUIRED FOR COVERING THE TAM WINDOW IS CALCULATED ACCORDING TO THE PITCH OF THE CONE BEAM SPIRAL CT SYSTEM AND THE ROW SPACING OF MULTIPLE ROWS OF DETECTORS

S62: IN A CASE THAT THE ROW NUMBER OF DETECTORS OF THE CONE BEAM SPIRAL CT SYSTEM IS LESS THAN THE MINIMUM ROW NUMBER OF DETECTORS, THE MISSING PROJECTION DATA IS COMPENSATED BY WEIGHTING THE COMPLEMENTARY PROJECTION DATA

S63: THE COMPLEMENTED PROJECTION DATA IS REARRANGED AS DATA OF PARALLEL BEAMS WITH A CONE ANGLE

S64: CONE-ANGLE COSINE WEIGHTING IS IMPLEMENTED ON THE REARRANGED DATA OF PARALLEL BEAMS, AND THEN ONE-DIMENSIONAL FILTERING IS IMPLEMENTED ON THE DATA ALONG A ROW DIRECTION OF VIRTUAL DETECTORS DEFINED WHEN THE PROJECTION DATA IS REARRANGED AS THE DATA OF PARALLEL BEAMS

S65: CONE-ANGLED PARALLEL BEAM BACK PROJECTION WITHOUT WEIGHTING IS IMPLEMENTED ON THE FILTERED DATA, TO OBTAIN RECONSTRUCTED IMAGES

Fig. 6

SPIRAL CT SYSTEMS AND RECONSTRUCTION METHODS

CROSS-REFERENCE TO RELATED APPLICATIONS

This application claims the benefit of the filing date under 35 U.S.C. §119(a)-(d) of Chinese Patent Application No.: 201410202941.3, filed May 14, 2014.

FIELD OF THE INVENTION

The embodiments of the present disclosure generally relate to radiation imaging, and in particular, to a Computed Tomography (CT) system with a large pitch and a reconstruction method thereof.

BACKGROUND

CT-type luggage security inspection systems have become an important measure for detecting explosives, and are widely applied in public places such as airports, stations or the like. The principle of the CT detection system is to obtain projection data of the luggage by scanning, obtaining tomographic images thereof by using a reconstruction algorithm, identifying explosives according to an identification algorithm, and giving an alarm. The scanning is implemented by rotating a slip ring installed with an X-ray source and detectors while the object travels on a belt, and therefore, the scanning orbit is a spiral orbit. In order to satisfy the requirements of the security inspection authorities for the pass rate of the luggage, the speed at which the belt travels must achieve a certain value, for example, 0.3 m/s-0.5 m/s. In order to collect complete projection data required for reconstructing images, it needs to increase the rotation speed of the slip ring or increase a row number of detectors. With respect to the slip ring, in consideration of the mechanical intensity and the stability, the rotation speed cannot be increased infinitely. On the other hand, in consideration of the limit value of the cone angle of the X-ray source and the hardware cost of the detectors, the row number of detectors also cannot be increased infinitely. In overall consideration of the various factors above, the most effective manner to improve the pass rate of the luggage is to increase the scanning pitch.

In recent years, a series of results have been achieved in the field of spiral CT reconstruction algorithms, for example, the Katsevich algorithm, the PI algorithm, the CB-FBP algorithm or the like. However, all of the algorithms need to satisfy a certain pitch condition, and when the pitch and the cone angle increase, it results in projection data missing, an error in the reconstructed result increasing, or even artifacts being introduced. In order to ensure that the quality of the images satisfies requirements, the pitch factor is generally no more than 1.5.

In the security inspection CT system, real time performance of the reconstruction algorithm is also an important index. In the reconstruction algorithm, filtering in a non-one-dimensional shift-invariant form, cone beam back projection with a distance weighting factor, solution of a large number of non-linear equations, and use of a large back projection angle range will result in inefficiency of the reconstruction algorithm, and such algorithms should be avoided. Therefore, some of the above reconstruction algorithms have steps that influence the efficiency of the algorithms, and are also primarily used in case the projection data is complete or redundant.

For these systems, a problem exists in that data is missed when operating at a large pitch and thus the related art described above cannot be directly applied to a CT system with a large pitch.

SUMMARY

In view of one or more problems in the related art, a spiral CT system and a reconstruction method thereof are proposed, which can satisfy requirements for image reconstruction in a condition of a large pitch.

In an aspect of the present disclosure, a reconstruction method of a cone-beam spiral Computed Tomography (CT) system is proposed, comprising steps of: calculating a minimum row number of detectors required for covering a Tam window according to a pitch of the cone-beam spiral CT system and a row spacing of multiple rows of detectors; compensating for the missing projection data by weighting the complementary projection data in a case that the row number of detectors of the cone-beam spiral CT system is less than the minimum row number of detectors; rebinning the cone beam data to cone parallel beam data; implementing cone-angle cosine weighting on the rebinned cone parallel data, and then implementing one-dimensional filtering on the data along a row direction of virtual detectors defined when the projection data is rebinned as the data of parallel beams; and implementing cone parallel beam back projection without weighting on the filtered data, to obtain reconstructed images.

In another aspect of the present disclosure, a cone-beam spiral Computed Tomography (CT) system is proposed, comprising: means for calculating a minimum row number of detectors required for covering a Tam window according to a pitch of the cone-beam spiral CT system and a row spacing of multiple rows of detectors; means for compensating for the missing projection data by weighting the complementary projection data in a case that the row number of detectors of the cone-beam spiral CT system is less than the minimum row number of detectors; means for rebinning the complemented projection data as data of parallel beams with a cone angle; means for implementing cone-angle cosine weighting on the rebinned cone parallel data, and then implementing one-dimensional filtering on the data along a row direction of virtual detectors defined when the projection data is rebinned as the data of parallel beams; and means for implementing cone parallel beam back projection without weighting on the filtered data, to obtain reconstructed images.

In some embodiments, with the above solutions, the speed of the belt can be increased by more than one time in a case that the existing area of the detectors and the existing speed of the slip ring are unchanged, thereby improving the pass rate of the luggage and maintaining the quality of the reconstructed images unchanged.

BRIEF DESCRIPTION OF THE DRAWINGS

For better understanding the present disclosure, the embodiments of the present disclosure will be described in detail according to the accompanying drawings below.

FIG. 5 illustrates a structural block diagram of a controller according to an embodiment of the present disclosure;

FIG. 6 illustrates a flowchart of a reconstruction method according to an embodiment of the present disclosure;

DETAILED DESCRIPTION OF THE EMBODIMENT(S)

The specific embodiments of the present disclosure will be described in detail below. It should be noted that the embodiments herein are used for illustration only, without limiting the present disclosure. In the description below, a number of specific details are explained to provide better understanding of the present disclosure. However, it is apparent to those skilled in the art that the present disclosure can be implemented without these specific details. In other instances, well known circuits, materials or methods are not described specifically so as not to obscure the present disclosure.

Throughout the specification, the reference to "one embodiment," "an embodiment," "one example" or "an example" means that the specific features, structures or properties described in conjunction with the embodiment or example are included in at least one embodiment of the present disclosure. Therefore, the phrases "in one embodiment," "in an embodiment," "in one example" or "in an example" occurred in various positions throughout the specification may not necessarily refer to the same embodiment or example. Furthermore, specific features, structures or properties may be combined into one or more embodiments or examples in any appropriate combination and/or sub-combination. Moreover, it should be understood by those skilled in the art that the term "and/or" used herein means any and all combinations of one or more listed items.

With respect to the case that the requirements for reconstruction in a condition of a large pitch cannot be satisfied in the related art, especially when the pitch factor is larger than 1.5, it is proposed in the embodiments of the present disclosure that data missing due to a large pitch is compensated by weighting the complementary projection data of the projection data obtained using the spiral CT system. After the data is complemented, the cone beam data is rebinned to cone parallel beam data, cone-angle cosine weighting and one-dimensional filtering are implemented on the rebinned cone parallel data, and the parallel beam back projection is finally implemented on the filtered data, to obtain the reconstructed images. In some embodiments, with the above method, the speed of the belt can be increased by more than one time such that the existing area of the detectors and the existing speed of the slip ring are unchanged, thereby improving the pass rate of the luggage and maintaining the quality of the reconstructed images unchanged.

Figure 1:
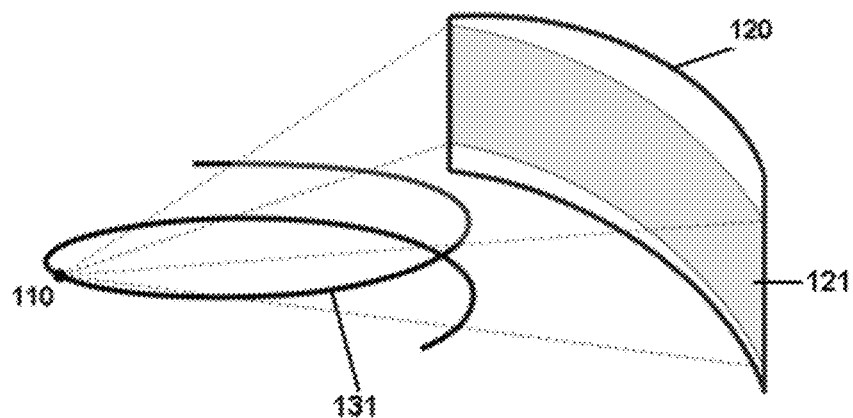
FIG. 1 illustrates a diagram of spiral orbit scanning in a CT system according to an embodiment of the present disclosure, wherein a gray area on the detectors represents a Tam window.

FIG. 1 illustrates a diagram of spiral orbit scanning in a CT system according to an embodiment of the present disclosure. As shown in FIG. 1, a rotational radius of an X-ray source 110 is defined as R, a distance a belt travels when a slip ring rotates in a circle (referred to as a pitch) is defined as h, a field angle of a fan beam of cylindrical equiangular detectors 120 is defined as $2\alpha_m$, and a distance from the X-ray source 110 to the detectors 120 is defined as D. A row number of the detectors 120 is $N_{row}$, and a row spacing is $s_{row}$. The pitch factor is defined as:

$$p = \frac{Dh}{RN_{row}s_{row}} \quad (1)$$

The circular rotation of the slip ring and the translation of the belt form a spiral orbit 131 due to a relative motion. In a coordinate system of the scanned object, a motion trajectory of the X-ray source may be expressed as:

$$r = \begin{pmatrix} R\cos\lambda \\ R\sin\lambda \\ h\frac{\lambda}{2\pi} \end{pmatrix} \quad (2)$$

In a case of a spiral scanning orbit, projection data required for accurate reconstruction is the projection data covered by the projection of two segments of the spiral line which are closest to each other on the detectors, i.e., Tam-Danielsson window (Tam window for short below) 121, as shown in FIG. 1. Thereby, a minimum row number of detectors required for covering the Tam window in a case that parameters such as the row spacing $s_{row}$ and the pitch h or the like are defined can be calculated as:

$$N_{row}^{Tam} = \frac{hD(\pi/2 + \alpha_m)}{\pi R s_{row} \cos\alpha_m} \quad (3)$$

According to the equation (3), a maximum pitch and a maximum pitch factor allowed by a CT system in which the row number of detectors, the row spacing and the fan angle are fixed can be derived reversely as:

$$h_{max} = \frac{\pi R N_{row} s_{row} \cos\alpha_m}{D(\pi/2 + \alpha_m)} \quad (4)$$

$$p_{max} = \frac{\pi \cos\alpha_m}{\pi/2 + \alpha_m}$$

For example, when the fan angle is $2\alpha_m=\pi/3$, the maximum pitch factor is 1.3.

Figure 2:
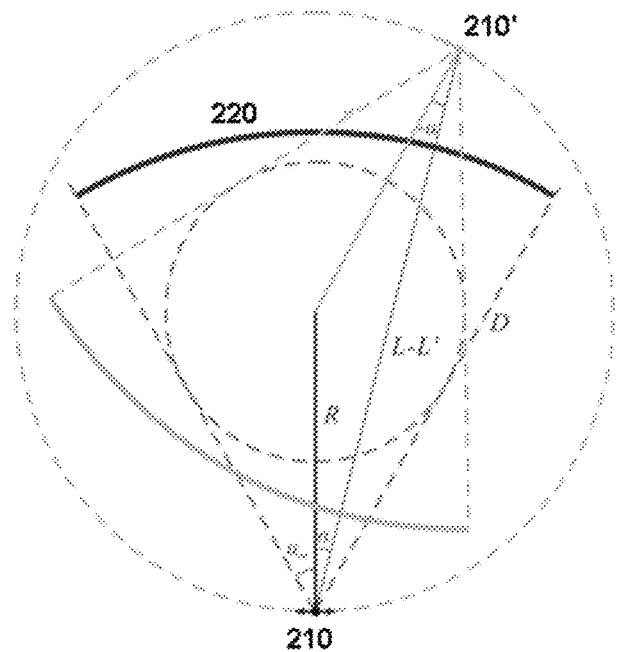
FIG. 2 illustrates definition of a pair of conjugate rays in fan beam scanning according to an embodiment of the present disclosure.

FIG. 2 illustrates definition of a pair of conjugate rays in fan beam scanning according to an embodiment of the present disclosure. As shown in FIG. 2, a rotational radius of an X-ray source 210 is defined as R, a distance a belt travels when a slip ring rotates in a circle (referred to as a pitch) is defined as h, a field angle of a fan beam of cylindrical equiangular detectors 220 is defined as $2\alpha_m$, and a distance from the X-ray source 210 to the detectors 220 is defined as D. In a case of two-dimensional fan beam scanning, two rays on the same straight line are referred to as a pair of conjugate rays L-L', i.e., a ray from the ray source 210 to a location 210' and a ray from the location 210' to the location 210 when the ray source is located in the location 210', as shown in FIG. 2. In a case of cone beam spiral scanning, there is no proper pair of conjugate rays; however, complementary projections in a similar relationship may be defined as:

$$P(\lambda, \alpha, s) \leftrightarrow P(\lambda \pm \pi - 2\alpha, -\alpha, s) \quad (5)$$

Thus, during back projection, the spiral reconstruction algorithm can implement redundant weighting or compensate for missing data by using the complementary projection data.

Figure 3:
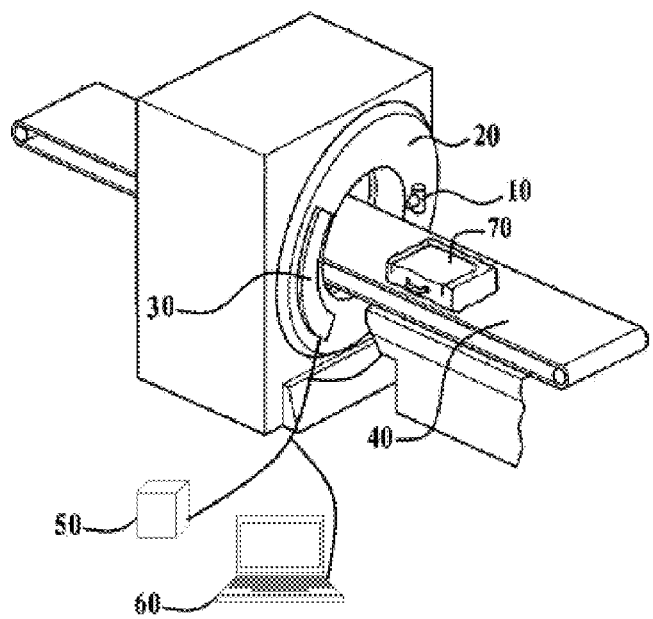
FIG. 3 is a structural diagram of a CT device according to an embodiment of the present disclosure.

FIG. 3 is a structural diagram of a CT device according to an embodiment of the present disclosure. As shown in FIG. 3, the CT device according to the present embodiment comprises a rack 20, a bearing member 40, a controller 50, a computer data processor 60 or the like. The rack 20 comprises a ray source 10 to emit an X-ray for inspection, for example, an X-ray machine, and a detection and collection apparatus 30. The bearing member 40 bears the inspected luggage 70 to pass through a scanned area between the ray source 10 and the detection and collection apparatus 30 of the rack 20, while the rack 20 rotates around the forward direction of the inspected luggage 70. In this way, the cone beam ray emitted from the ray source 10 can transmit through the inspected luggage 70 to implement CT scanning on the inspected luggage 70.

The detection and collection apparatus 30 includes for example detectors and data collectors in an integrated modular structure, such as multiple rows of detectors, to detect rays transmitting through the inspected materials to obtain an analog signal, and convert the analog signal into a digital signal, so as to output projection data of the inspected luggage 70 with respect to the X-ray. The controller 50 is configured to control various parts of the whole system to operate synchronously. The computer data processor 60 is configured to process the data collected by the data collector, process and reconstruct the data, and output a result.

As shown in FIG. 3, the ray source 10 may be placed on one side of an inspected object, and the detection and collection apparatus 30 is placed on the other side of the inspected luggage 70, including detectors and data collectors, to obtain transmission data and/or multi-angle projection data of the inspected luggage 70. The data collector comprises a data amplification and shaping circuit, which may operate in a (current) integration manner or a pulse (counting) manner. A data output cable of the detection and collection apparatus 30 is connected to the controller 50 and the computer data processor 60, to store the collected data in the computer data processor 60 according to a trigger command.

Figure 4:
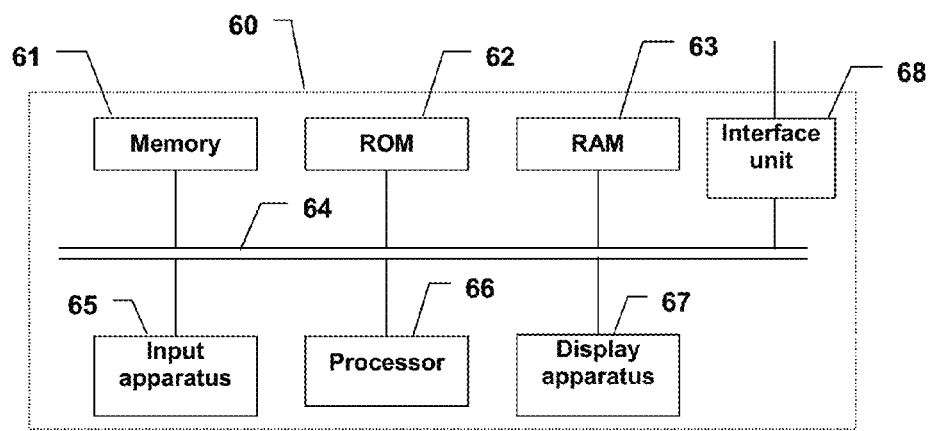
FIG. 4 illustrates a structural block diagram of a computer data processor illustrated in FIG. 3.

FIG. 4 illustrates a structural block diagram of a computer data processor 60 illustrated in FIG. 3. As shown in FIG. 4, the data collected by the data collector is stored in a memory 61 through an interface unit 68 and a bus 64. A Read-Only Memory (ROM) 62 has configuration information and programs of the computer data processor stored therein. A Random-Access Memory (RAM) 63 is configured to temporarily store various data in the operation process of a processor 66. In addition, the memory 61 also has computer programs for processing data stored therein. An internal bus 64 is configured to connect the memory 61, the ROM 62, the RAM 63, the input apparatus 65, the processor 66, the display apparatus 67, and the interface unit 68 as described above.

After a user inputs an operation command through an input apparatus 65 such as a keyboard, a mouse or the like, instruction codes of the computer program command the processor 66 to execute a predetermined data reconstruction algorithm, and after obtaining a data processing result, display the result on a display apparatus 67 such as a Liquid Crystal Display (LCD) display or the like, or directly output the processing result in a form of hard copy such as printing.

FIG. 5 illustrates a structural block diagram of a controller according to an embodiment of the present disclosure. As shown in FIG. 5, the controller 50 comprises a controller unit 51 configured to control the ray source 10, the bearing member 40 and the detection and collection apparatus 30 according to an instruction from the computer 60; a trigger signal generation unit 52 configured to generate a trigger command for triggering actions of the ray source 10, the detection and collection apparatus 30 and the bearing member 40 under the control of the control unit; a first driving device 53 configured to drive the bearing member 40 to transfer the inspected luggage 70 according to the trigger command generated by the trigger signal generation unit 52 under the control of the control unit 51; and a second driving device 54 configured to drive the rack 20 to rotate according to the trigger command generated by the trigger signal generation unit 52 under the control of the control unit 51. The projection data obtained by the detection and collection apparatus 30 is stored in the computer 60 for reconstruction of CT tomographic images, so as to obtain data of the tomographic images of the inspected luggage 70. According to other embodiments, the above CT imaging system may also be a dual-energy CT system, that is, the X-ray source 10 of the rack 20 may emit two rays, i.e., a high-energy ray and a low-energy ray, and after the detection and collection apparatus 30 detects projection data at different energy levels, the computer data processor 60 implements dual-energy CT reconstruction, to obtain equivalent atomic numbers and equivalent electron density data of various tomographic images of the inspected luggage 70.

FIG. 6 illustrates a flowchart of a reconstruction method according to an embodiment of the present disclosure. As shown in FIG. 6, in step S61, a minimum row number of detectors required for covering the Tam window is calculated according to the pitch of the cone beam spiral CT system and the row spacing of multiple rows of detectors. For example, a minimum row number of detectors $N_{row}^{Tam}$ required for covering the Tam window is calculated according to parameters such as the pitch, the row spacing or the like.

Figure 7:
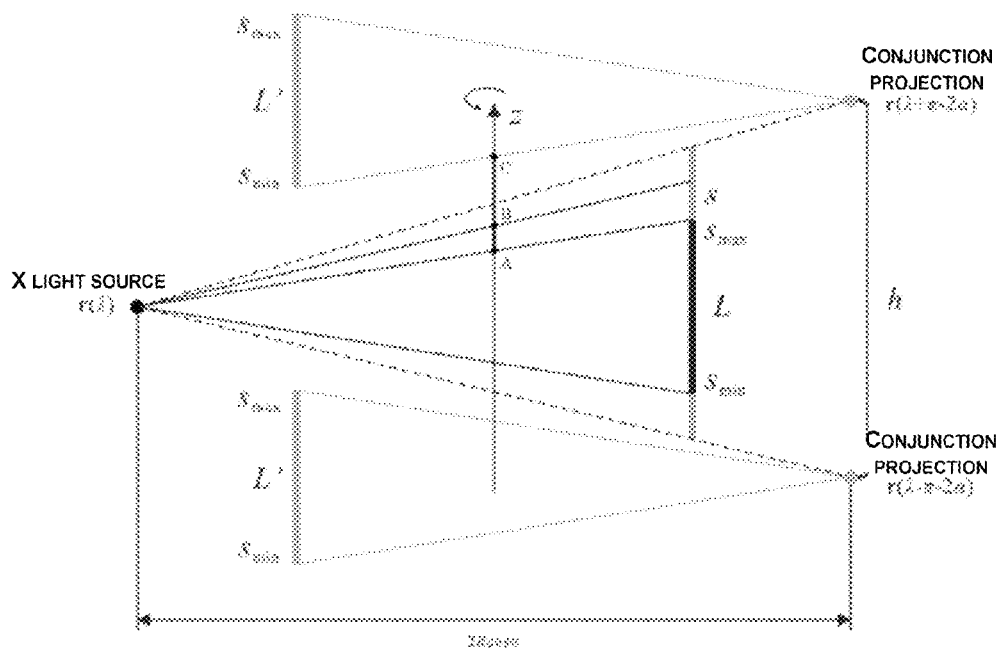
FIG. 7 illustrates a diagram of conjugate projection interpolation in spiral orbit scanning according to an embodiment of the present disclosure.

In step S62, in a case that the row number of detectors of the cone beam spiral CT system is less than the minimum row number of detectors, the missing projection data is compensated by weighting the complementary projection data. For example, if the actual row number of detectors is less than $N_{row}^{Tam}$, the missing data is compensated by using complementary projection. As shown in FIG. 7, there are two conditions as follows:

1) when $s > s_{max}$, $$P(\lambda, \alpha, s) = (1 - w_1) \Box P(\lambda, \alpha, s_{max}) + w_1 \Box P(\lambda + \pi - 2\alpha, -\alpha, s_{min}) \quad (6)$$

$$w_1 = \frac{AB}{AC} = \frac{s - s_{max}}{\frac{hD(\pi - 2\alpha)}{2\pi R \cos\alpha} - (s_{max} - s_{min})}$$

2) similarly, when $s < s_{min}$, $$P(\lambda, \alpha, s) = (1 - w_2) \Box P(\lambda, \alpha, s_{min}) + w_2 \Box P(\lambda - \pi - 2\alpha, -\alpha, s_{max}) \quad (7)$$

$$w_2 = \frac{s_{min} - s}{\frac{hD(\pi + 2\alpha)}{2\pi R \cos\alpha} - (s_{max} - s_{min})}$$

wherein, s represents a row (cone angle) directional coordinate of the detectors, α represents a column (fan angle) directional coordinate of the detectors, λ represents a projection angle, $s_{min}$ represents a minimum row (cone angle) directional coordinate value of the detectors, $s_{max}$ represents a maximum row (cone angle) directional coordinate value of the detectors, R represents a rotational radius of an X-ray source, h represents a distance a belt travels when a slip ring rotates in a circle, i.e., a pitch, and D represents a distance from the X-ray source to cylindrical detectors.

Figure 8:
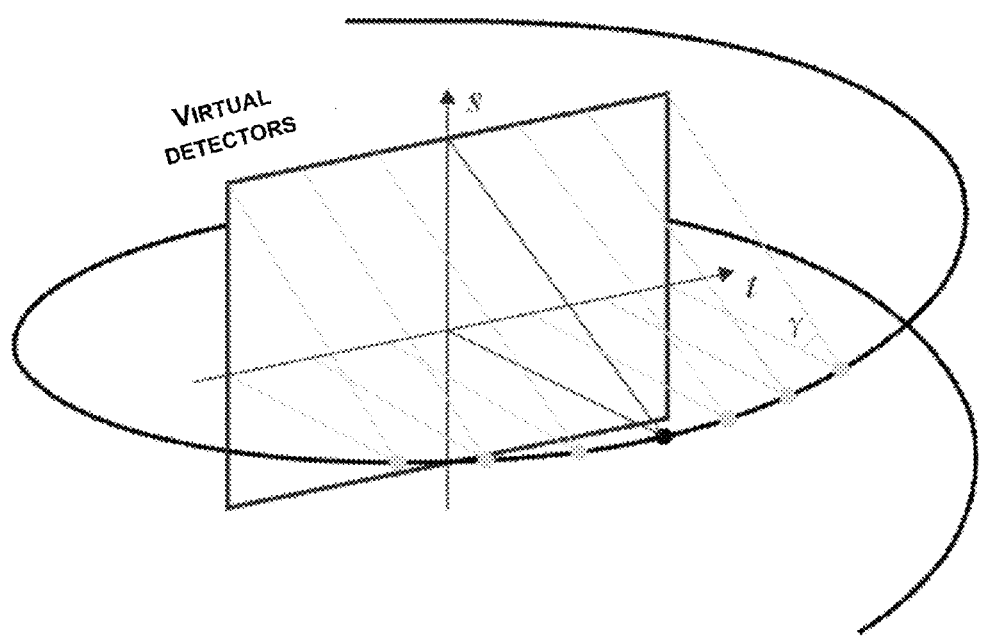
FIG. 8 illustrates a diagram of rebinned parallel beams with a cone angle and virtual detectors.

In step S63, the complemented cone beam data P (λ,α,s) is rebinned to cone parallel beam data for example data of parallel beams with a cone angle $P^p$ (λ,t,s). The rebinned virtual detectors are defined in a rectangular region across the center of rotation and parallel to the z axis, which has a width equal to a diameter 2R sin $α_m$ of the field covered by the fan angle of the real cylindrical detectors, as shown in FIG. 8.

In step S64, cone-angle cosine weighting is firstly implemented on the rebinned data, and then one-dimensional filtering is implemented on the data, wherein the filtering direction is along the row direction of the virtual detectors. As the filtering process is in a one-dimensional shift-invariant form, filtering may be implemented by using a fast Fourier transform. The R-L convolution kernel in the parallel beam filtering and back projection algorithm is selected as the filter kernel:

$$P^f(\lambda,t,s)=(P^p(\lambda,t,s)\cos \gamma)*g(t) \quad (8)$$

In step S65, cone parallel beam back projection without weighting is implemented, to obtain reconstructed images:

$$f(x,y,z)=\int_{2\pi z/h-\pi/2}^{2\pi z/h+\pi/2}P^f(\lambda,t,s)d\lambda \quad (9)$$

With the method according to the present embodiment, the speed of the belt can be increased by more than one time in a case that the existing area of the detectors and the existing speed of the slip ring are unchanged, thereby improving the pass rate of the luggage and maintaining the quality of the reconstructed images unchanged. On the other hand, with the method according to the present disclosure, the design of the existing CT system can be modified in a particular usage occasion to suitably reduce the row number of detectors, thereby reducing the system cost.

For example, the X-ray source has a rotational radius of 50 cm, the distance from the source to the detectors is 80 cm, the detectors has a fan angle of 60°, the row number of detectors is 32, and the row spacing is 1.5 mm. If it needs to satisfy the requirements for collection of complete projection data, the maximum pitch factor is 1.3, and the corresponding maximum pitch is 3.9 cm. With the method according to the present disclosure, the maximum pitch may be increased to 6 cm, and the pitch factor is 2.

Figure 9:
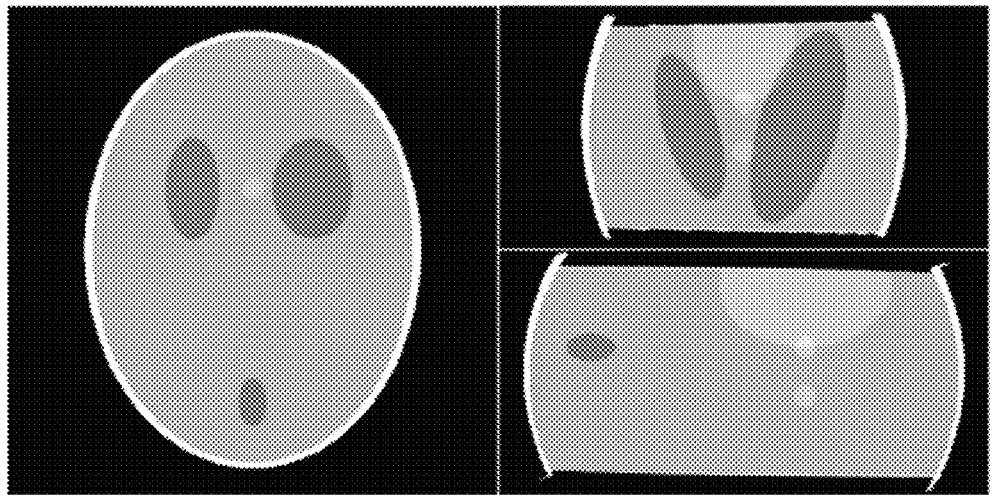
FIG. 9 illustrates a reconstructed result when the pitch is 3.9 cm according to a specific embodiment of the present disclosure.
Figure 10:
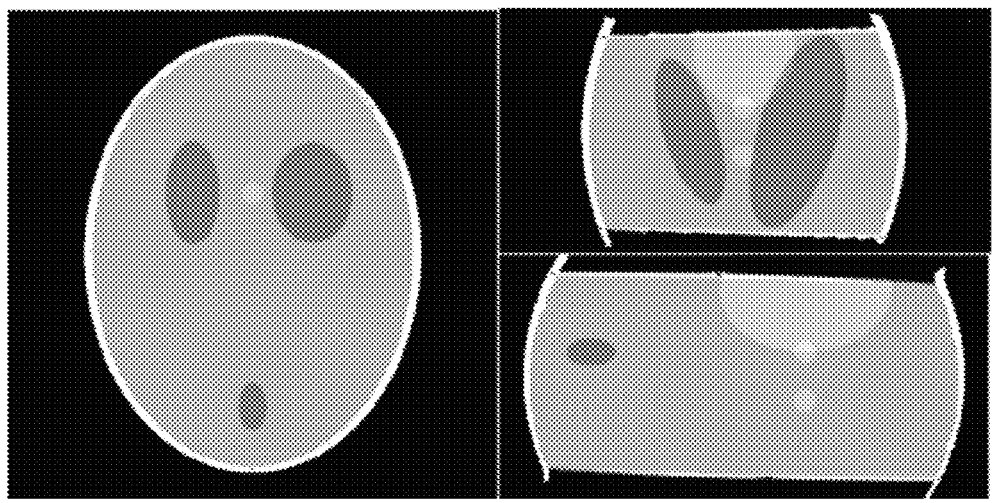
FIG. 10 illustrates a reconstructed result when the pitch is 6 cm according to a specific embodiment of the present disclosure.

FIG. 9 illustrates a reconstructed result when the pitch is 3.9 cm according to a specific embodiment of the present disclosure. FIG. 10 illustrates a reconstructed result when the pitch is 6 cm according to a specific embodiment of the present disclosure. It can be seen from the figures that the quality of the reconstructed images is maintained while improving the scanning speed.

According to some embodiments, the speed of the belt can be further improved in the condition of the existing hardware such as detectors, slip ring or the like, so as to improve the pass rate, which can be applied in the field of security inspection such as explosive inspection, drug inspection or the like. In addition, the proposed method of compensating for missing data using complementary projection is applicable to a condition that the projection data is incomplete, and can still ensure the quality of the reconstructed images when the pitch factor is larger than 1.5. At the same time, the reconstruction algorithm proposed in the embodiment is in a shift-invariant filtering form, uses parallel beam back projection without a distance weighting factor, uses a minimum back projection angle range which is 180 degree, and needs not to solve a group of non-linear equations. Thus, the method has lower complexity relative to the related art, and can satisfy the requirements of the security inspection for real time performance.

The foregoing detailed description has set forth various embodiments of the reconstruction method and spiral CT system via the use of diagrams, flowcharts, and/or examples. In a case that such diagrams, flowcharts, and/or examples contain one or more functions and/or operations, it will be understood by those skilled in the art that each function and/or operation within such diagrams, flowcharts or examples may be implemented, individually and/or collectively, by a wide range of structures, hardware, software, firmware, or virtually any combination thereof. In one embodiment, several portions of the subject matter described in the embodiments of the present disclosure may be implemented via Application Specific Integrated Circuits (ASICs), Field Programmable Gate Arrays (FPGAs), Digital Signal Processors (DSPs), or other integrated formats. However, those skilled in the art will recognize that some aspects of the embodiments disclosed herein, in whole or in part, may be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware would be well within the skill of those skilled in the art in ray of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Versatile Disk (DVD), a digital tape, a computer memory, etc.; and a transmission type medium such as a digital and/or an analog communication medium (e.g., a fiber optic cable, a waveguide, a wired communications link, a wireless communication link, etc.).

While the present disclosure has been described with reference to several typical embodiments, it is apparent to those skilled in the art that the terms are used for illustration and explanation purpose and not for limitation. The present disclosure may be practiced in various forms without departing from the spirit or essence of the present disclosure. It should be understood that the embodiments are not limited to any of the foregoing details, and shall be interpreted broadly within the spirit and scope as defined by the following claims. Therefore, all of modifications and alternatives falling within the scope of the claims or equivalents thereof are to be encompassed by the claims as attached.

What is claimed is:

1. A reconstruction method of a cone-beam spiral Computed Tomography (CT) system, comprising steps of:
  calculating a minimum row number of detectors required for covering a Tam window according to a pitch of the cone-beam spiral CT system and a row spacing of multiple rows of detectors;
  compensating for the missing projection data by weighting the complementary projection data in a case that the row number of detectors of the cone-beam spiral CT system is less than the minimum row number of detectors;
  rebinning the cone beam data to cone parallel beam data;
  implementing cone-angle cosine weighting on the rebinned cone parallel data, and then implementing one-dimensional filtering on the data along a row direction of virtual detectors defined when the projection data is rebinned as the data of parallel beams; and
  implementing cone parallel beam back projection without weighting on the filtered data, to obtain reconstructed images.

2. The method according to claim 1, wherein the step of compensating for the missing projection data by weighting the complementary projection data comprises:
  when $s > s_{max}$, $$P(\lambda, \alpha, s) = (1 - w_1) \Box P(\lambda, \alpha, s_{max}) + w_1 \Box P(\lambda + \pi - 2\alpha, -\alpha, s_{min})$$

$$w_1 = \frac{AB}{AC} = \frac{s - s_{max}}{\frac{hD(\pi - 2\alpha)}{2\pi R \cos\alpha} - (s_{max} - s_{min})}$$

when $s < s_{min}$, $$P(\lambda, \alpha, s) = (1 - w_2) \Box P(\lambda, \alpha, s_{min}) + w_2 \Box P(\lambda - \pi - 2\alpha, -\alpha, s_{max})$$

$$w_2 = \frac{s_{min} - s}{\frac{hD(\pi + 2\alpha)}{2\pi R \cos\alpha} - (s_{max} - s_{min})}$$

wherein, s represents a row (cone angle) directional coordinate of the detectors, α represents a column (fan angle) directional coordinate of the detectors, λ represents a projection angle, $s_{min}$ represents a minimum row (cone angle) directional coordinate value of the detectors, $s_{max}$ represents a maximum row (cone angle) directional coordinate value of the detectors, R represents a rotational radius of an X-ray source, h represents a distance a belt travels when a slip ring rotates in a circle, i.e., a pitch, and D represents a distance from the X-ray source to cylindrical detectors.

3. The method according to claim 1, wherein the one-dimensional filtering uses a R-L convolution kernel.

4. A cone-beam spiral Computed Tomography (CT) system, comprising:
  means for calculating a minimum row number of detectors required for covering a Tam window according to a pitch of the cone-beam spiral CT system and a row spacing of multiple rows of detectors;
  means for compensating for the missing projection data by weighting the complementary projection data in a case that the row number of detectors of the cone-beam spiral CT system is less than the minimum row number of detectors;
  means for rebinning the complemented projection data as cone parallel beam data;
  means for implementing cone-angle cosine weighting on the rebinned data of parallel beams, and then implementing one-dimensional filtering on the data along a row direction of virtual detectors defined when the projection data is rebinned as the data of parallel beams; and
  means for implementing cone parallel beam back projection without weighting on the filtered data, to obtain reconstructed images.

5. The system according to claim 4, wherein the means for compensating for the missing projection data by weighting the complementary projection data comprises means for:
  when $s > s_{max}$, $$P(\lambda, \alpha, s) = (1 - w_1) \Box P(\lambda, \alpha, s_{max}) + w_1 \Box P(\lambda + \pi - 2\alpha, -\alpha, s_{min})$$

$$w_1 = \frac{AB}{AC} = \frac{s - s_{max}}{\frac{hD(\pi - 2\alpha)}{2\pi R \cos\alpha} - (s_{max} - s_{min})}$$

when $s < s_{min}$, $$P(\lambda, \alpha, s) = (1 - w_2) \Box P(\lambda, \alpha, s_{min}) + w_2 \Box P(\lambda - \pi - 2\alpha, -\alpha, s_{max})$$

$$w_2 = \frac{s_{min} - s}{\frac{hD(\pi + 2\alpha)}{2\pi R \cos\alpha} - (s_{max} - s_{min})}$$

wherein, s represents a row (cone angle) directional coordinate of the detectors, a represents a column (fan angle) directional coordinate of the detectors, λ represents a projection angle, $s_{min}$ represents a minimum row (cone angle) directional coordinate value of the detectors, $s_{max}$ represents a maximum row (cone angle) directional coordinate value of the detectors, R represents a rotational radius of an X-ray source, h represents a distance a belt travels when a slip ring rotates in a circle, i.e., a pitch, and D represents a distance from the X-ray source to cylindrical detectors.

* * * * *

UNITED STATES PATENT AND TRADEMARK OFFICE
CERTIFICATE OF CORRECTION

PATENT NO. : 9,466,137 B2
APPLICATION NO. : 14/708866
DATED : October 11, 2016
INVENTOR(S) : Zhang et al.

It is certified that error appears in the above-identified patent and that said Letters Patent is hereby corrected as shown below:

In Column 6, Lines 53-65, should read as follows:

when $s > s_{max}$, $$P(\lambda,\alpha,s) = (1-w_1)*P(\lambda,\alpha,s_{max})$$
$$+w_1*P(\lambda+\pi-2\alpha,-\alpha,s_{min})$$

$$w_1 = \frac{AB}{AC} = \frac{s-s_{max}}{\frac{hD(\pi-2\alpha)}{2\pi R\cos\alpha} - (s_{max}-s_{min})}$$

when $s < s_{min}$, $$P(\lambda,\alpha,s) = (1-w_2)*P(\lambda,\alpha,s_{min})$$
$$+w_2*P(\lambda-\pi-2\alpha,-\alpha,s_{max})$$

$$w_2 = \frac{s_{min}-s}{\frac{hD(\pi+2\alpha)}{2\pi R\cos\alpha} - (s_{max}-s_{min})}$$

Signed and Sealed this
Twenty-seventh Day of March, 2018

Andrei Iancu
*Director of the United States Patent and Trademark Office*

In Column 9, Lines 28-41, should read as follows:

when $s > s_{max}$, $$P(\lambda,\alpha,s) = (1-w_1) \cdot P(\lambda,\alpha,s_{max})$$
$$+ w_1 \cdot P(\lambda + \pi - 2\alpha, -\alpha, s_{min})$$

$$w_1 = \frac{AB}{AC} = \frac{s - s_{max}}{\frac{hD(\pi - 2\alpha)}{2\pi R \cos\alpha} - (s_{max} - s_{min})}$$

when $s < s_{min}$, $$P(\lambda,\alpha,s) = (1-w_2) \cdot P(\lambda,\alpha,s_{min})$$
$$+ w_2 \cdot P(\lambda - \pi - 2\alpha, -\alpha, s_{max})$$

$$w_2 = \frac{s_{min} - s}{\frac{hD(\pi + 2\alpha)}{2\pi R \cos\alpha} - (s_{max} - s_{min})}$$

In Column 10, Lines 28-41, should read as follows:

when $s > s_{max}$, $$P(\lambda,\alpha,s) = (1-w_1) \cdot P(\lambda,\alpha,s_{max})$$
$$+ w_1 \cdot P(\lambda + \pi - 2\alpha, -\alpha, s_{min})$$

$$w_1 = \frac{AB}{AC} = \frac{s - s_{max}}{\frac{hD(\pi - 2\alpha)}{2\pi R \cos\alpha} - (s_{max} - s_{min})}$$

when $s < s_{min}$, $$P(\lambda,\alpha,s) = (1-w_2) \cdot P(\lambda,\alpha,s_{min})$$
$$+ w_2 \cdot P(\lambda - \pi - 2\alpha, -\alpha, s_{max})$$

$$w_2 = \frac{s_{min} - s}{\frac{hD(\pi + 2\alpha)}{2\pi R \cos\alpha} - (s_{max} - s_{min})}$$